United States Patent
Qiu et al.

(10) Patent No.: US 6,383,517 B1
(45) Date of Patent: *May 7, 2002

(54) PROCESS FOR PREPARING SOLID FORMULATIONS OF LIPID-REGULATING AGENTS WITH ENHANCED DISSOLUTION AND ABSORPTION

(75) Inventors: Yihong Qiu, Gurnee, IL (US); Venkatramana M. Rao, Lawrence, KS (US); Kevin R. Engh, Mundelein; Thomas L. Reiland, Gages Lake, both of IL (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/240,516

(22) Filed: Jan. 29, 1999

(51) Int. Cl.[7] .............................. A61K 9/20; A61K 9/48
(52) U.S. Cl. .................. 424/464; 424/465; 424/451; 424/452; 514/772.3; 514/777; 514/778; 514/784

(58) Field of Search ................................ 424/464, 465, 424/451, 452, 489

(56) References Cited

U.S. PATENT DOCUMENTS

| 4,058,552 | A | 11/1977 | Mieville ...................... 560/52 |
| 4,739,101 | A | 4/1988 | Bourgogne et al. ........... 560/61 |
| 4,800,007 | A | 1/1989 | Boyer ......................... 424/482 |
| 4,895,726 | A | 1/1990 | Curtet et al. ................. 424/456 |
| 4,961,890 | A | 10/1990 | Boyer ......................... 264/113 |
| 5,645,856 | A | 7/1997 | Lacy et al. .................. 424/455 |

FOREIGN PATENT DOCUMENTS

| EP | 0793958 | 2/1997 |
| WO | 8201649 | 5/1982 |

*Primary Examiner*—James M. Spear
(74) *Attorney, Agent, or Firm*—Rockey, Milnamow & Katz, Ltd.

(57) ABSTRACT

A process for preparing a solid formulation of a lipid-regulating agent comprising dissolving said lipid-regulating agent particles in a surfactant solution, premixing an excipient, wet granulating the mixture, drying the mixture and forming a finished dosage form.

14 Claims, 2 Drawing Sheets

PROCESS FOR PREPARING SOLID FORMULATIONS OF LIPID-REGULATING AGENTS WITH ENHANCED DISSOLUTION AND ABSORPTION

FIELD OF THE INVENTION

The present invention relates to a new process for preparing solid formulations of lipid-regulating agents with enhanced dissolution and absorption characteristics.

BACKGROUND OF THE INVENTION

2-[4-(4-chlorobenzoyl)phenoxy]-2-methyl-propanoic acid, 1-methylethylester, also known as fenofibrate, is representative of a broad class of compounds having pharmaceutical utility as lipid-regulating agents. More specifically, this compound is part of a lipid-regulating agent class of compounds commonly known as fibrates, and is disclosed in U.S. Pat. No. 4,058,552.

Fenofibrate has been prepared in several different formulations, c.f., U.S. Pat. Nos. 4,800,079 and 4,895,726. U.S. Pat. No. 4,895,726 discloses a co-micronized formulation of fenofibrate and a solid surfactant.

U.S. Pat. No. 4,961,890 discloses a process for preparing a controlled release formulation containing fenofibrate in an intermediate layer in the form of crystalline microparticles included within pores of an inert matrix. The formulation is prepared by a process involving the sequential steps of dampening said inert core with a solution based on said binder, then projecting said fenofibrate microparticles in a single layer onto said dampened core, and thereafter drying, before said solution based on said binder dissolves said fenofibrate microparticles, and repeating said three steps in sequence until said intermediate layer is formed.

European Patent Application No. EP0793958A2 discloses a process for producing a fenofibrate solid dosage form utilizing fenofibrate, a surface active agent and polyvinyl pyrrolidone in which the fenofibrate particles are mixed with a polyvinyl pyrrolidone solution. The thus obtained mixture is granulated with an aqueous solution of one or more surface active agents, and the granules thus produced are dried.

PCT Publication No. WO82/01649 discloses a fenofibrate formulation having granules that are comprised of a neutral core that is a mixture of saccharose and starch. The neutral core is covered with a first layer of fenofibrate, admixed with an excipient and with a second microporous outer layer of an edible polymer.

U.S. Pat. No. 5,645,856 discloses the use of a carrier for hydrophobic drugs, including fenofibrate, and pharmaceutical compositions based thereon. The carrier comprises a digestible oil and a pharmaceutically-acceptable surfactant component for dispersing the oil in vivo upon administration of the carrier, which comprises a hydrophilic surfactant, said surfactant component being such as not to substantially inhibit the in vivo lipolysis of the digestible oil.

The prior art processes obtained small particles of fenofibrate by the use of co-micronization steps. These resulting formulations may not have maximized dissolution characteristics.

It is an object of the present invention to provide small particles of lipid-regulating agents, more preferably fenofibrate, having enhanced dissolution and absorption characteristics than those particles of such agents prepared by the prior art techniques with the need of micronizing the lipid-regulating agent.

SUMMARY OF THE INVENTION

The present invention is directed to a process for preparing a solid formulation of a lipid-regulating agent with enhanced dissolution and absorption characteristics.

This process comprises dissolving the lipid-regulating agent in a surfactant solution, premixing an excipient, wet granulating the lipid-regulating agent/surfactant solution and the premix, drying the resulting mixture, and optionally sizing the dried granules and forming a finished dosage form.

The mixture may be granulated by techniques well-known in the art, preferably by a fluidized bed or by means of a low shear or high shear mixer.

The finished oral dosage form may be prepared by techniques well-known to those skilled in the art by sizing the mixture, dry blending the resultant particles with excipients into the finished oral dosage form, preferably as a tablet or capsule.

The formulation thus produced may be administered directly as a granulated product, diluted into an appropriate vehicle for administration, encapsulated into hard gelatin shells or capsules for administration, or administered by other means obvious to those skilled in the art.

DETAILED DESCRIPTION OF THE INVENTION

The bulk lipid-regulating agent can be prepared by any available method, as for example the compound fenofibrate may be prepared by the procedure disclosed in U.S. Pat. No. 4,658,552, or the procedure disclosed in U.S. Pat. No. 4,739,101, both herein incorporated by reference.

The lipid-regulating agent is then dissolved in a surfactant solution, such as for example, docusate sodium, in a solvent, such as for example, acetone or methylene chloride, or a cosolvent such as acetone-water in amounts ranging from 1 part by weight surfactant solutions: 0.032 parts by weight fenofibrate to 1 part by weight surfactant solutions: 1.16 parts by weight fenofibrate. Other suitable surfactants include sorbitan esters, polysorbates, lecithin, and all pharmaceutically-acceptable anionic, cationic, ampholytic, nonionic surfactants. Other suitable solvents include ethanol, methanol, ether, ethyl acetate, isopropyl alcohol, and tetrahydofuran.

A premix of excipients is prepared. Suitable excipients include, for example, lactose, starch, polyvinyl pyrrolidone, magnesium stearate, or other pharmaceutically-acceptable excipients may be used.

The lipid-regulating agent/surfactant solution and excipient premix are then mixed together. The resulting mixture is then granulated, for example, in a fluidized bed or a low or high shear mixer and dried by well-known solvent evaporation techniques, as for example, spray drying, fluid bed, spinning disk drying, or evaporation under reduced pressure. The resultant material may then be sized, if necessary and formulated into a finished dosage form, for example, a tablet or capsule by conventional techniques such as direct compression or other means.

The invention will be understood more clearly from the following non-limiting representative examples:

EXAMPLE 1

Fenofibrate (12 g) and docusate sodium (3 g) were dissolved in 20 ml methylene chloride. Lactose anhydrous (32.5 g) and sodium starch glycolate (2 g) were premixed. The premix was granulated with above solution. The wet granules were tray dried in an oven at 40 C. The dried granules were sieved through a 100 mesh screen and filled into a hard gelatin capsule.

In vitro dissolution rate of the capsules were compared with that of the reference, Lipanthyl, the marketed capsule product, which contains the same amount of the active. USP apparatus II was used for testing. The test conditions were: paddle speed=75 rpm; dissolution medium=100 mM SDS solution; temperature=37 C. Dissolution samples were analyzed by an HPLC method.

Figure 1:
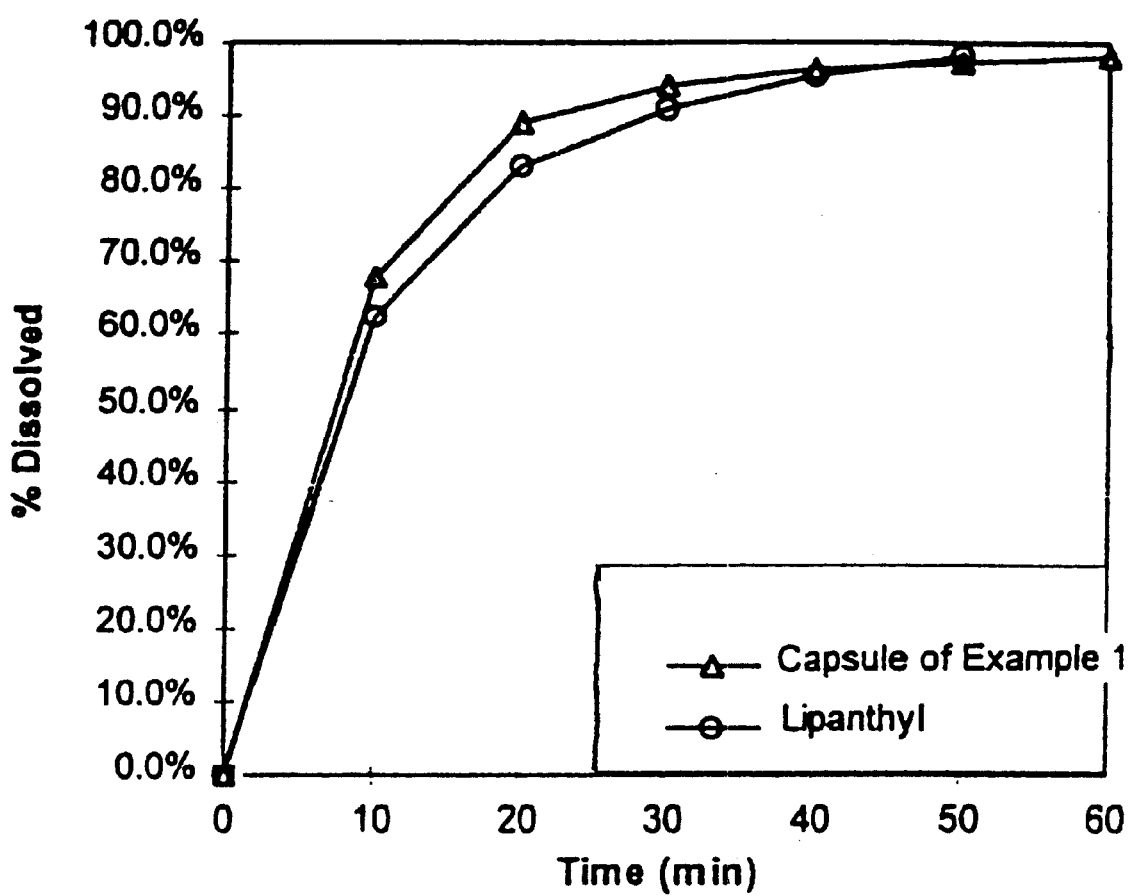
FIG. 1 is a graph showing the dissolution characteristics of a representative composition prepared by the process of the present invention and a prior art composition.

In vitro dissolution profiles of a capsule containing milled fenofibrate, the reference capsule (Lipanthyl) and capsule from the current invention are shown in FIG. 1. The data indicates that the dissolution rate of the capsules of the present invention are higher than the reference capsules. Based on U.S. Pat. No. 4,895,726, in vitro dissolution result can be correlated to the in vivo absorption in humans. Thus, equivalent or increased dissolution in vitro can result in bioavailability equivalent to or improved over the reference in humans.

EXAMPLE 2

Fenofibrate (15 g) and docusate sodium (3 g) were dissolved in 45 ml acetone. Lactose anhydrous (29 g) and crospovidone (3 g) were premixed. The premix was mixed with above solution. The wet mass was tray dried in an oven at 30 C.

The dried solid was milled and sieved through a 100 mesh screen. The small particles were filled into a hard gelatin capsule.

In vitro dissolution rate of the capsules were compared with that of the reference, Lipanthyl, the marketed capsule product, which contains the same amount of the active. USP apparatus II was used for testing. The test conditions were: paddle speed=75 rpm; dissolution medium=100 mM SDS solution; temperature=37 C. Dissolution samples were analyzed by an HPLC method.

Figure 2:
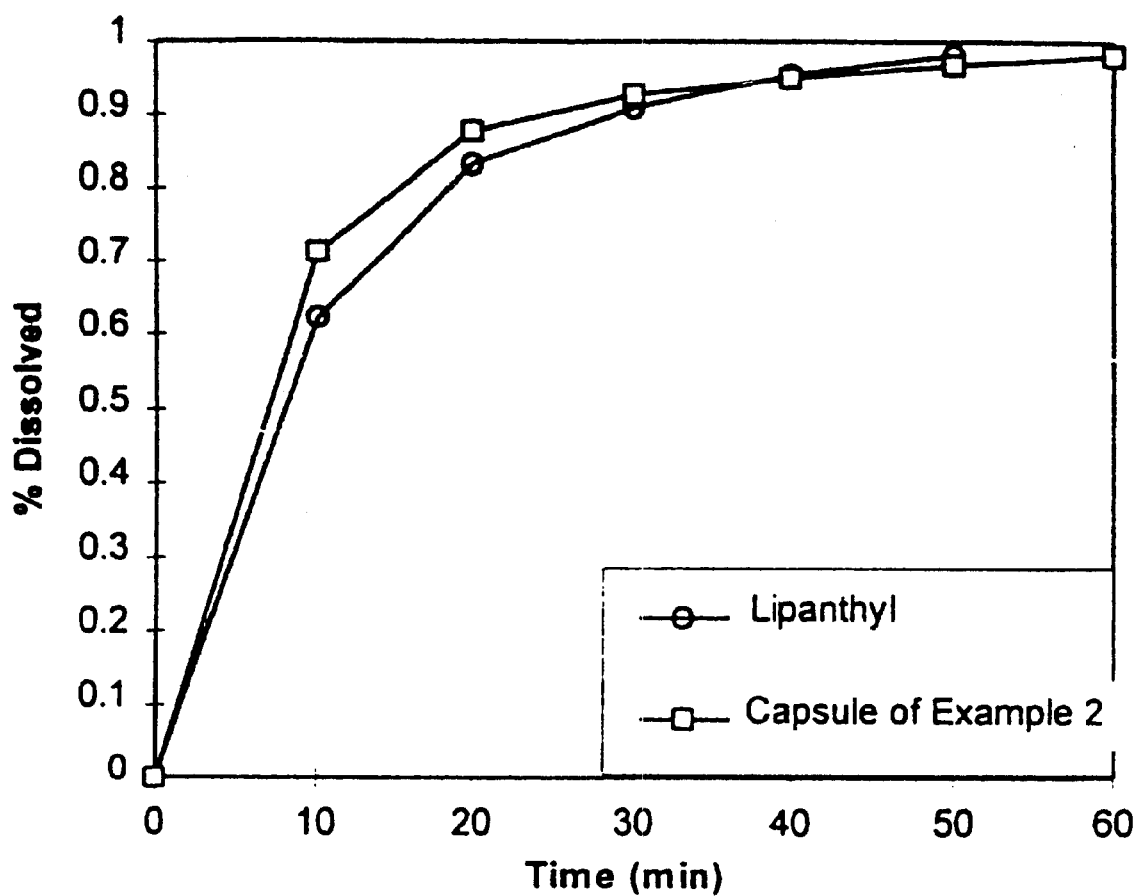
FIG. 2 is a graph showing the dissolution characteristics of another representative composition prepared by the process of the present invention and a prior art composition.

In vitro dissolution profiles of the reference capsules and capsules from the present invention are shown in FIG. 2. Preliminary data indicate that dissolution rate of the capsules of the present invention are higher than the reference capsules. Based on U.S. Pat. No. 4,895,726, in vitro dissolution result can be correlated to the in vivo absorption in humans. Thus, equivalent or increased dissolution in vitro can result in bioavailability equivalent to or improved over the reference in humans.

What is claimed is:

1. A process for preparing a solid formulation of a fibrate comprising the steps of:

dissolving said fibrate in a surfactant solution;

premixing excipients;

mixing the excipient premix with the fibrate dissolved in surfactant solution;

wet granulating the resulting fibrate/surfactant and excipient mixture;

drying the mixture optionally in the presence of one or more excipients, and optionally forming a finished dosage form.

2. A process of claim 1 wherein the fibrate is fenofibrate.

3. A process of claim 1 where the mixture is dried by solvent evaporation.

4. A process of claim 1 where the mixture is dried by fluid bed, spinning disk drying or evaporation under reduced pressure.

5. A process of claim 1 where the surfactant is sodium docusate.

6. A process of claim 1 further comprising forming a finished dosage form.

7. A process of claim 6 where the finished dosage form is a tablet.

8. A process of claim 6 where the finished dosage form is a capsule.

9. The process of claim 1 wherein excipients are selected from the group consisting of lacotse, starch, polyvinyl pyrrolidone and magnesium stearate.

10. A process as in claim 1 where the mixture is granulated in a fluidized bed or by means of a low shear or high shear mixer.

11. A composition prepared by the process of claim 1.

12. A composition prepared by the process of claim 2.

13. A method for treating hyperlipidemia comprising the administration of a formulation prepared by the process of claim 1.

14. A method for treating of hyperlipidemia comprising the administration of a formulation prepared by the process of claim 2.

* * * * *